United States Patent [19]

Matsuo et al.

[11] Patent Number: 5,336,759
[45] Date of Patent: Aug. 9, 1994

[54] BIOLOGICALLY ACTIVE PEPTIDE DERIVED FROM FROG (FROG CNP)

[75] Inventors: Hisayuki Matsuo, 5-15-141, 5-chome, Onoharahigashi, Minoo-shi, Osaka; Kenji Kangawa, Miyazaki; Naoto Minamino, Osaka, all of Japan

[73] Assignees: Suntory Limited; Hisayuki Matsuo, Osaka, Japan

[21] Appl. No.: 754,958

[22] Filed: Sep. 4, 1991

[30] Foreign Application Priority Data

Sep. 7, 1990 [JP] Japan .................. 2-238294

[51] Int. Cl.⁵ .................. C07K 7/00; A61K 37/02
[52] U.S. Cl. .................. 530/326
[58] Field of Search .................. 530/326; 514/13

[56] References Cited

U.S. PATENT DOCUMENTS 4,904,763  2/1990  Matsuo et al. .................. 530/324
5,114,923  5/1992  Seilhamer et al. .................. 514/12

OTHER PUBLICATIONS

Yoshihara et al. Biochem. Biophys. Res. Commun. (1990) 173(2) 591-8.
Minamino et al. Pept. Chem. (1991) 28 367-72.
Yoshihara et al, "Chemical Abstracts", Columbus, Apr. 1, 1991, vol. 114, No. 13; Minamino et al, Chemical Abstracts, Columbus, Aug. 19, 1991, vol. 115 No. 7; Nakao et al, Chemical Abstracts, Columbus, Nov. 19, 1990, vol. 113 No. 21.
Minamino et al; C-Type Natriuretic Peptide (CNP); Biochemical and Biophysical Research Communications; vol. 168, No. 2, 1990.
Minamino et al.; N-Terminally Extended Form of C--Type Natriuretic Peptide (DNP-53) Identified in Porcine Brain; vol. 170, No. 2, 1990.

Primary Examiner—Merrell C. Cashion, Jr.
Assistant Examiner—Carol A. Salata
Attorney, Agent, or Firm—Cushman, Darby & Cushman

[57] ABSTRACT

A novel peptide that exhibits a natriuretic action and a vasodepressor activity, and hence, that is applicable for a diagnostic reagent. The novel peptide is manufactured by tile procedure of genetic engineering as well as by the methods of purification from frog brains or by chemical synthesis.

1 Claim, 5 Drawing Sheets

Fig. 5

| | | | | | | |
|---|---|---|---|---|---|---|
| A type | S-L-R-R-S-S- | C-F-G-G-R-M-D-R-I-G-A-Q-S-G-L-G-C | -N-S-F-R- Y | porcine α-ANP |
| | S-L-R-R-S-S- | C-F-G-G-R-I-D-R-I-G-A-Q-S-G-L-G-C | -N-S-F-R- -Y | rat α-ANP |
| | S-S-D- | C-F-G-S-R-I-D-R-I-G-A-Q-S-G-M-G-C | -G- -R-R-F | frog ANP-24 |
| B type | S-P-K-T-M-R-D-S-G- | C-F-G-R-R-L-D-R-I-G-S-L-S-G-L-G-C | -N-V-L-R-R-Y | porcine BNP-32 |
| | M-M-R-D-S-G- | C-F-G-R-R-I-D-R-I-G-S-L-S-G-M-G-C | -N-G-S-R-K-N | chicken α-NP |
| C type | G-L-S-K-G- | C-F-G-L-K-L-D-R-I-G-S-M-S-G-L-G-C | | porcine CNP |
| | G-Y-S-R-G- | C-F-G-V-K-L-D-R-I-G-A-F-S-G-L-G-C | | frog CNP |

1    10    20

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Tyr  Ser  Arg  Gly  Cys  Phe  Gly  Val  Lys  Leu  Asp  Arg  Ile  Gly
 1                    5                         10                        15
Ala  Phe  Ser  Gly  Leu  Gly  Cys
                     20
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ser Leu Arg Arg Ser Ser Cys Phe Gly Gly Arg Met Asp Arg Ile
1               5                   10                  15

Gly Ala Gln Ser Gly Leu Gly Cys Asn Ser Phe Arg Tyr
                20                  25
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ser Leu Arg Arg Ser Ser Cys Phe Gly Gly Arg Ile Asp Arg Ile
1               5                   10                  15

Gly Ala Gln Ser Gly Leu Gly Cys Asn Ser Phe Arg Tyr
                20                  25
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser Ser Asp Cys Phe Gly Ser Arg Ile Asp Arg Ile Gly Ala Gln
1               5                   10                  15

Ser Gly Met Gly Cys Gly Arg Arg Phe
                20
```

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ser Pro Lys Thr Met Arg Asp Ser Gly Cys Phe Gly Arg Arg Leu
1               5                   10                  15

Asp Arg Ile Gly Ser Leu Ser Gly Leu Gly Cys Asn Val Leu Arg
                20                  25                  30

Arg Tyr
```

( 2 ) INFORMATION FOR SEQ ID NO:6:

( i ) SEQUENCE CHARACTERISTICS:
        ( A ) LENGTH: 29 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

Met Met Arg Asp Ser Gly Cys Phe Gly Arg Arg Ile Asp Arg Ile
1               5                   10                  15

Gly Ser Leu Ser Gly Met Gly Cys Asn Gly Ser Arg Lys Asn
                20              25

(2) INFORMATION FOR SEQ ID NO:7:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

Gly Leu Ser Lys Gly Cys Phe Gly Leu Lys Leu Asp Arg Ile Gly
1               5                   10                  15

Ser Met Ser Gly Leu Gly Cys
                20

BIOLOGICALLY ACTIVE PEPTIDE DERIVED FROM FROG (FROG CNP)

FIELD OF THE INVENTION

The present invention relates to a novel biologically active frog peptide which has a natriuretic action and exhibits vasodepressor activity. More particularly, the invention relates to a process for isolating, identifying and utilizing a novel biologically active peptide which belongs to C-type natriuretic peptide.

PRIOR ART

Recently, various peptides, which are known as natriuretic peptides (NP), have been identified and isolated from the atrium and brain of mammals. At present, these NPs can be classified into one of three types, A-type natriuretic peptide (ANP), B-type natriuretic peptide (BNP) and C-type natriuretic peptide (CNP), on the basis of the homology of the primary amino acid sequences and the structures of precursors thereof.

Among them, ANP and BNP are also referred to as an atrial natriuretic peptide and a brain natriuretic peptide, respectively, since ANP and BNP were first isolated and identified from the atrium and brain, respectively (Matsuo, H. and Nakazato, H., *Endocrinol. Metab. Clin. North Am.*, 16, 43, 1987; Sudoh, T. et al., *Nature*, 332, 78, 1988). However, it has become apparent that ANP exists not only in the atrium but also in the brain, and BNP likewise exists not only in the brain but also in the atrium. Moreover, both ANP and BNP exhibit a natriuretic action and a vasodepressor activity. Therefore, it has been clarified that ANP and BNP respectively act as a hormone which regulates the homeostatic balance of body fluid volume and blood pressure of mammals, and at a neuro transmitter in the brain.

Whereas, CNP was isolated very recently from a porcine brain and characterized as a new type of NP which does not belong to any of ANP and BNP (Sudoh, et al., *Biochem. Biophys. Res. Commun.*, 168, 863, 1990). CNP consists of 22 amino acid residues, and contains 2 cystein residues like ANP and BNP. Thus, the two cystein residues form an intramolecular disulfide bond, and the molecule has a cyclic structure consisted of 17 amino acid residues. Furthermore, the primary amino acid sequence constructing the cyclic structure of CNP was found to be highly homologous to those of ANP and BNP. The structure of CNP is characteristic in that it has no tail, while both ANP and BNP have a tail which consists of several amino acid residues added to the C-terminal of said cyclic structure. In other words, tile C-terminal of CNP ends with a cystein residue. Thus, it has turned out that the structure of CNP differs from that of ANP or BNP in spite of the homology in other respects, and that CNP is a new type of NP since CNP exhibits a natriuretic action and a vasodepressor activity, and further shows a specific activity higher than ANP or BNP in relaxation of intestinum rectum specimens of chickens.

Therefore, it has been understood that various NP peptides, which can be classified into at least three different types, exist in mammals at present, and that these peptides participate in regulating the homeostatic balance of body fluid volume and blood pressure. Until now, details of CNP in terms of the distribution in the body and the physiological function were not as clear as in ANP and BNP.

On the other hand, the existence of NP peptides in non-mammal vertebrates has already been confirmed. Until now, however, only frog ANP, chicken NP and eel ANP have been Isolated and characterized. The information about NP in non-mammals is less comprehensive than that for mammals (Sakata, J., Kangawa, K. and Matsuo H. *Biochem. Biophys. Res. Commun.*, 155, 1338–1345, 1988; Miyata, A., Minamino, N., Kangawa, K. and Matsuo, H. *Biochem. Biophys. Res. Commun.*, 155, 1330–1337, 1988; Takei, Y., Takahashi, A., Watanabe, T. X., Nakajima, K. and Sakakibara, S. *Biochem. Biophys. Res. Commun.*, 164, 537–543, 1989).

From amphibia, several biologically active peptides have been found which are analogous to certain peptides of mammals (Erspamer, V. and Melchiori, P. *Trends Pharmacol. Sci.*, 1, 391–395, 1980; Nakajima, T. *Trends Pharmacol. Sci.*, 2, 202–205, 1981). In searching for unidentified peptides in pig medulla spinalis, in fact, the present inventors have successfully found a peptide which was analogous to that of amphibia (Minamino, N., Kangawa, K. and Matsuo, H. *Biochem. Biophys, Res. Commun.*, 114, 541–548, 1983; Miniamino, N., Kangawa, K. and Matsuo, H. *Biochem. Biophys. Res. Commun.*, 119, 14–20, 1984; Minamino, N., Sudoh, T., Kangawa, K. and Matsuo, H. *Peptides*, 6 (Suppl. 3), 245–248, 1985).

Therefore, as in the case of mammals, it is probable that different types of NPs exist in amphibia in addition to the well known frog ANP (this corresponds to mammal ANP). Until now, however, isolation and characterization of a novel peptide from amphibia have not been reported except for frog ANP.

SUMMARY OF THE INVENTION

An object of the present invention is to isolate and characterize a novel NP from frog in addition to frog ANP, and to establish a method of providing the novel NP.

BRIEF DESCRIPTION OF THE DRAWINGS

FIG. 5 is an illustration of the amino acid sequences of the different types of ANP, BNP and CNP, showing the homology of the primary amino acid sequences of these peptides. (see SEQ ID NO:2, SEQ ID NO:3, SEQ ID NO:4, SEQ ID NO:5, SEQ ID NO:6, and SEQ ID NO:7).

DETAILED DESCRIPTION OF THE INVENTION

The present inventors searched for a novel NP from a frog brain. In this research the biological activity was monitored by relaxation In chicken rectum because they had noticed that the assay was relatively easy and reliable in the measurement of the biological activity of NPs when they previously isolated and purified mammal NPs.

Figure 3:
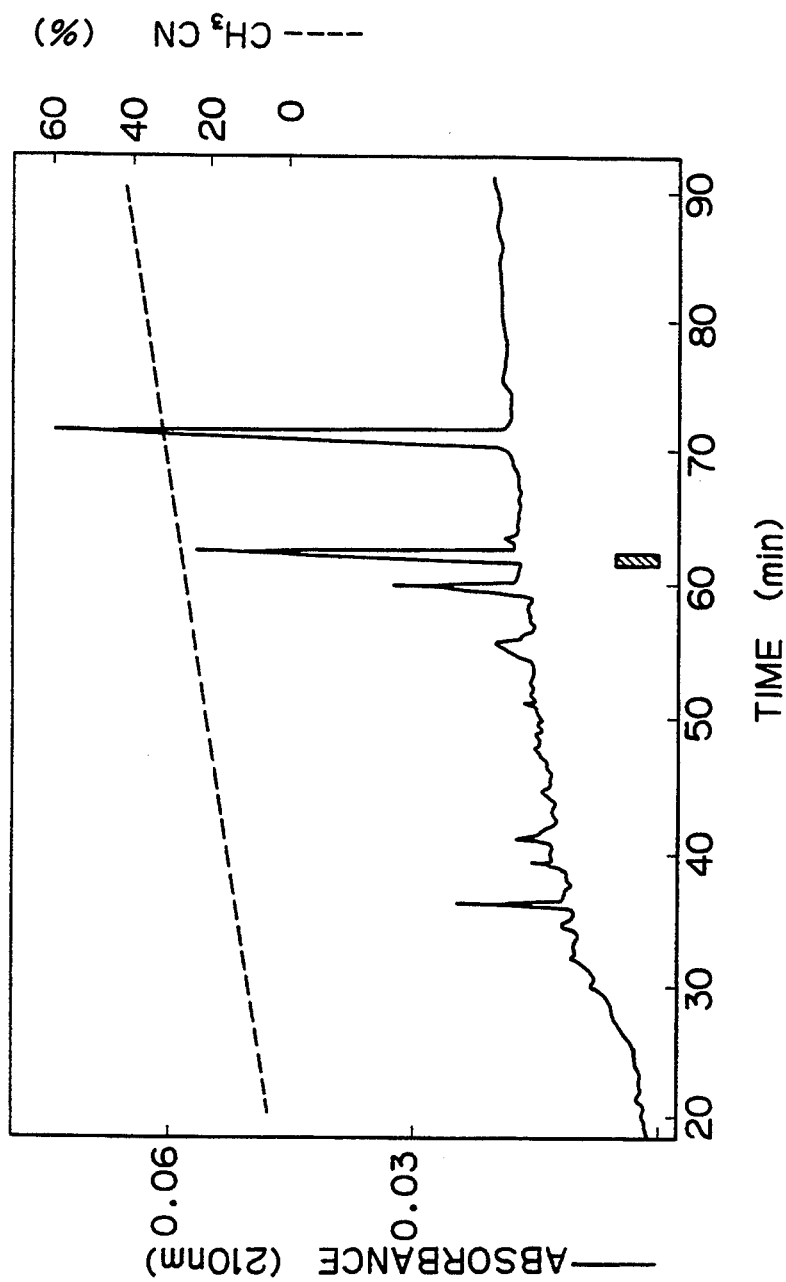
FIG. 3 is a graph showing the elution pattern and the relaxant activity in chicken rectum of each fraction when the active fraction, eluted from 36 to 39 minutes in the CM cation exchange HPLC in FIG. 2, was further purified by a reverse phase HPLC with a chemcosorb 30DS-H column.

A peptide having a relaxant activity in the bioassay using the specimen of chicken rectum was successfully purified as a single, pure substance as shown in FIG. 3 by homogenizing a frog brain in a suitable acidic solution such as glacial acetic acid, followed by a combination of different methods which arc commonly used in the purification of peptides, thus providing the purified fraction of a peptide having a molecular weight of about 3,000, using positive reaction in said bioassay as the measure of the desired peptide.

A sample of the purified peptide was then reduced, the cystein residues were carboxymethylated and the amino acid sequence of this peptide was determined. As a result, it was found to be a peptide consisting of 22 amino acid residues. Furthermore, by the determination of the primary amino acid sequence, it was found to be a novel peptide having the following structure:

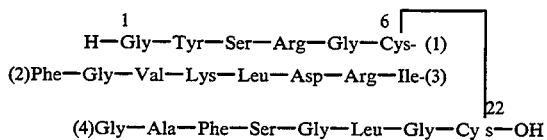

wherein (1) and (2), (3) and (4) directly bind, and the cystein residues (Cys) at positions 6 and 22 form an intramolecular disulfide bond (see SEQ ID NO.:1).

The novel peptide will be hereinafter referred to as fCNP (frog C-type natriuretic peptide).

The novel peptide fCNP was determined to be a novel peptide which belongs to CNP by comparing both the amino acid sequence and the structure with those of the known NPs which are classified into one of three types (see FIG. 5). Namely, fCNP consists of 22 amino acid residues like known CNPs, and does not have a C-terminal tail structure in keeping with the structural characteristic of CNP. Moreover, fCNP was found to be the most homologous to CNP when the amino acid sequence of fCNP was compared with ANP, BNP and CNP. Actually, 17 out of 22 amino acid residues in the primary amino acid sequence of fCNP were identical to CNP. Furthermore, the nature (such as the basicity and the hydrophobicity of amino acids) of the remaining five amino acid residues was substantially identical between fCNP and CNP. In addition, fCNP exhibited a natriuretic action and a vasodepressor activity in rats.

From these observations, fCNP was determined to be a novel peptide which belongs to CNP, resulting in the completion of the present invention.

Now that the structure of fCNP has been disclosed herein, fCNP may be manufactured by a genetic engineering method as well as the method shown in the present specification wherein fCNP is purified from frog brains, and further by use of chemical syntheses: In addition, since fCNP exhibits a significant natriuretic action and a vasodepressor activity, fCNP is expected to be applicable for drugs.

The following Examples are provided to further illustrate the present invention.

EXAMPLE 1

Isolation and purification of fCNP from frog brain

Figure 1:
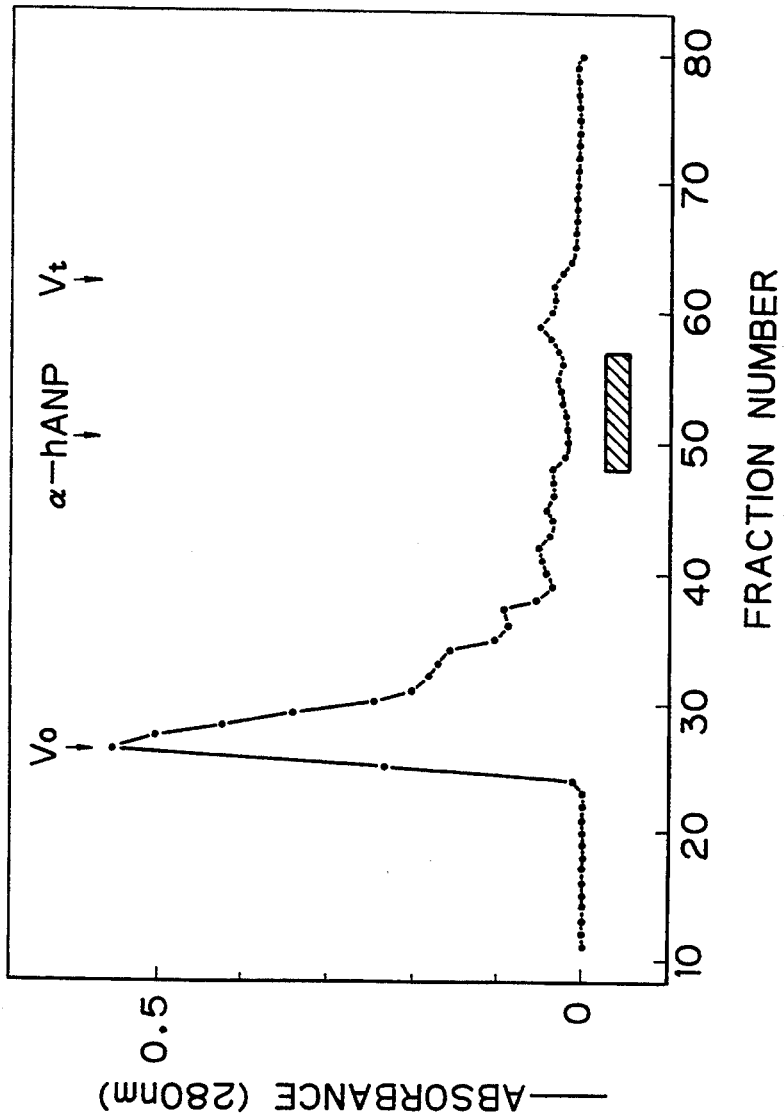
FIG. 1 is a graph showing the elution pattern and the relaxant activity in chicken rectum of each fraction when the fraction (SP-III) from frog brain extract was further fractionated with Sephadex G-50.

Brain sections weighing 47 grams were removed from 157 frogs, and, after- being cut into pieces, were treated with ten times the volume (V/W) of boiled water for 8 min to inactivate proteases. After cooling, glacial acetic acid was added up to a final concentration of 1M, and the tissue was homogenized for 5 min with a Polytron mixer. Subsequently, the homogenate was divided into a residual fraction and a supernatant fraction by centrifugation (14,500×g, 35 min). The supernatant was diluted with twice volume of water, and applied to a reverse phase C-18 column (90 ml Chemco LC-SORB SPW-C-ODS). After washing the column with 0.5M acetic acid, peptides which adsorbed on the column were eluted with 60% acetonitrile ($CH_3CN$) containing 0.1% trifluoroacetic acid (TFA). The eluate was concentrated and applied to an ion exchange chromatography using a SP-Sephadex C-25 column ($H^+$-form 10 ml) equalibrated with 1M acetic acid. Peptides which adsorbed on the column were eluted with 1M acetic acid, 2M pyridine and then 2M pyridine-acetic acid (pH 5.0). The eluted fractions, which will hereafter be referred to as SP-I, SP-II and SP-III, were freeze-dried, separately. A 40 mg portion (dry weight) of the obtained SP-III fraction was subjected to gel filtration using a Sephadex G-50 column (fine, 1.8×134 cm; Pharmacia). The gel filtration pattern is shown in FIG. 1. The solvent was 1M acetic acid, the fraction size was 5.0 ml/tube, and the flow rate was 10.0 ml/h. In FIG. 1, the box with slant lines indicates fractions (fraction numbers 49-57) which exhibited relaxant activity in chicken rectum.

The active fractions were freeze-dried, and further purified by HPLC using a CM cation exchanger (TSK gel Cr4-2SW: 4.6×250 mm, Tosoh). Using the following solvents (A) and (B), the elution was performed with linear density gradients in which the ratio of (A): (B) changed 50:50 to 0:100 for 20 min at a flow rate of 1.0 ml/h.

(A) 10 mM $HCOONH_4$ (pH 6.6):$CH_3CN$=90:10 (V/V)
(B) 1.0 mM $HCOONH_4$ (pH 6.6):$CH_3CN$=90:10 (V/V)

Figure 2:
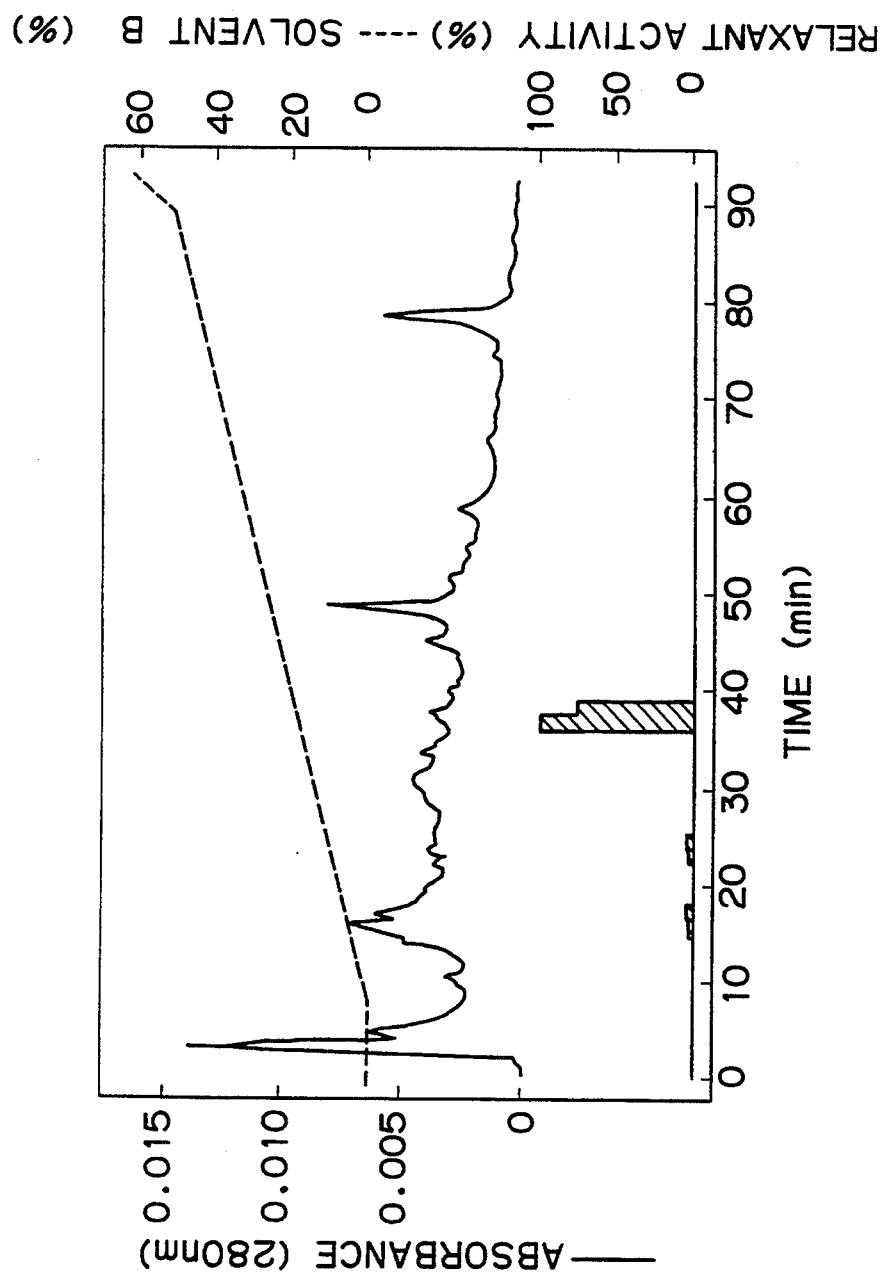
FIG. 2 is a graph showing the elution pattern and the relaxant activity in chicken rectum of each fraction when the active fraction, eluted from the Sephadex G-50 column in FIG. 1, was further purified by a CM cation exchange HPLC.

The elution pattern is shown in FIG. 2. In this chromatography, most of the relaxant activity in chicken rectum was eluted in elution time 36-39 min, and weak peaks were observed in elution times 15-18 min and 22.5-25.5 min.

The fractions, which were eluted in 36-39 min, and exhibited a relaxant activity in chicken rectum, were further purified by a reverse phase HPLC using a chemcosorb 30DS-H column (8.0×75 mm, chemco). Using following solvents (A) and (B), the elution was performed with a linear density gradient from (A) to (B) for 120 min at a flow rate of 20 ml/min.

(A) $H_2O$:$CH_3CN$:10% TFA=90:10:1 (V/V)
(B) $H_2O$:$CH_3CN$:10% TFA=40:60:1 (V/V)

The elution pattern is shown in FIG. 2. Relaxant activity in chicken rectum was observed in only the black-boxed portion in the figure.

A substantially pure peptide could be obtained by further subjecting the active fractions to a reverse phase HPLC using μ-bondasphere C-18 (3.9×150 mm, 300 A, Waters). The yield of the purified fCNP, as estimated on the basis of the results of amino acid analysis, was 920 pmol.

EXAMPLE 2

Determination of the structure of fCNP

A. S-carboxymethylation of fCNP

The purified fCNP which was obtained in Example 1 was incubated with 20 mM DTT in a 0.5M Tris-HCl buffer, pH 8.5 at 37° C. for 4 hours, and then S-carboxymethylated fCNP, i.e., (RCM) fCNP was obtained following the treatment with sodium monoiodoacetic acid, added at 60 mM, for 20 min.

The (RCM) fCNP was subjected to a reverse phase HPLC using μ-Bondasphere C-18 (3.9×150 mm, 300 A, Waters), and purified by elution over 60 min at a flow rate of 1.0 ml/min with a linear density gradient of 10–60% acetonitrile.

B. Determination of amino acid composition of (RCM) fCNP

About 200 pmol of (RCM) fCNP, which was obtained in Example 2A, was hydrolyzed by the treatment with 6N HCl containing 0.1% phenol and 0.02% 2-mercaptoethanol at 110° C. for 20 hours. Then, the amino acid composition of (RCM) fCNP was determined by an amino acid analyzer (L-83.5, Hitachi). From the results shown in Table 1, fCNP was found to consist of 22 amino acid residues including 2 cystein residues.

Table 1 shows the amino acid composition of (RCM) fCNP. The values in parentheses indicate integers nearest to the measured values. CmCys indicates a S-carboxymethyl cystein.

TABLE 1

| (RCM) fCNP | | |
|---|---|---|
| CmCys | 1.84 | (2) |
| Asp | 1.18 | (1) |
| Ser | 2.15 | (2) |
| Gly | 6.05 | (6) |
| Ala | 0.98 | (1) |
| Val | 1.02 | (1) |
| Ile | 0.98 | (1) |
| Leu | 2.00 | (2) |
| Tyr | 0.97 | (1) |
| Phe | 1.87 | (2) |
| Lys | 1.07 | (1) |
| Arg | 1.98 | (2) |
| Total | | (22) |

C. Determination of primary amino acid sequence of (RCM) fCNP

Figure 4:
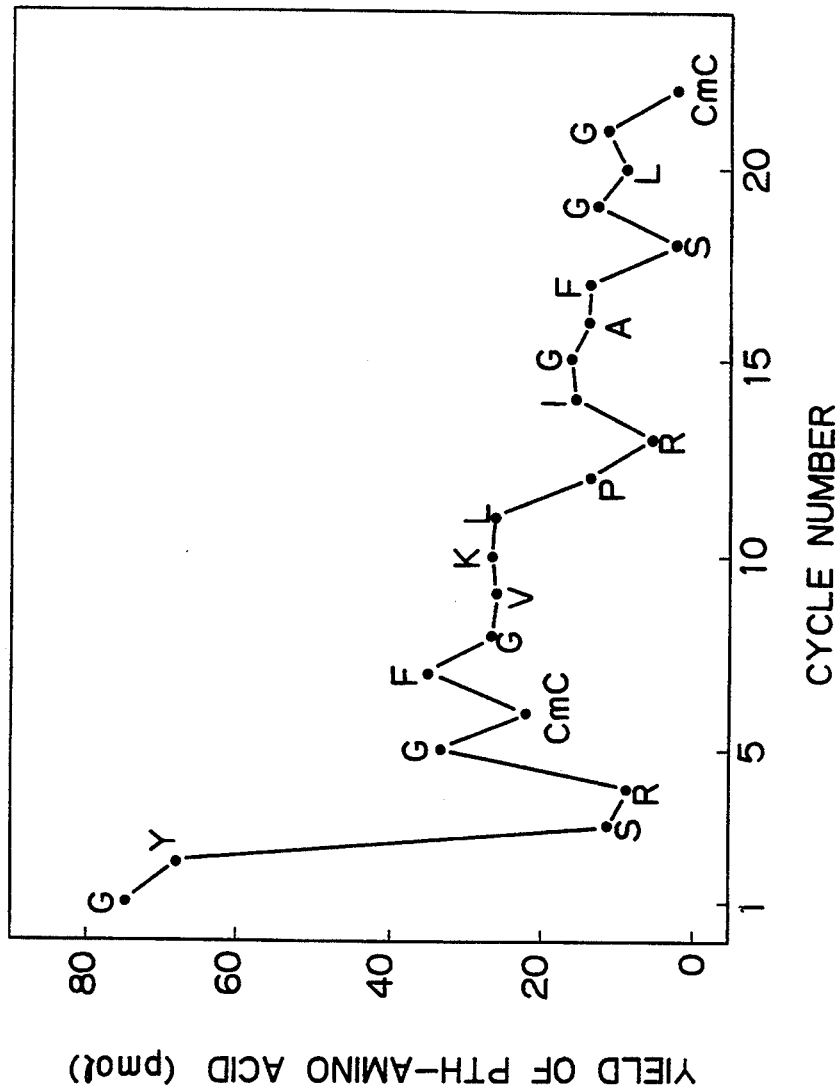
FIG. 4 is a graph showing the amino acid sequence and the yield of PTH-amino acid in each cycle in the sequence analysis of (RCM) fCNP by Edman degradation.

About 200 pmol of (RCM) fCNP, which was purified in Example 2A, was applied to an amino acid sequencer (Applied Biosystems 470A/120A), and the primary amino acid sequence was analyzed by Edman degradation. The results are shown in FIG. 4. In FIG. 4, each amino acid residue is expressed by a capital letter code, and Cm indicates a S-carboxymethyl cystein residue. Based on these results, the primary amino acid sequence of (RCM) fCNP was determined (see FIG. 5).

D. Chemical synthesis of fCNP and determination of the manner of the S-S bond In accordance with the primary amino acid sequence determined in Example 2C, a peptide having the primary amino acid sequence of fCNP was synthesized by the solid phase method using a peptide synthesizer (Applied Biosystems 430A). In the synthesis, 4-methylbenzyl group was used as a protective group for cystein residues. After complete deprotection with HF, an intramolecular S—S bond was formed by treating the SH groups in the cystein residues at positions 6 and 22 with $K_3Fe(CN)_6$. The structure of the resulted fCNP was confirmed by amino acid analysis and amino acid sequence analysis. Since the synthetic fCNP showed the same elution time as the natural fCNP obtained in Example 1, and also exhibited a positive relaxant activity in chicken rectum, the structure of fCNP was finally determined as follows:

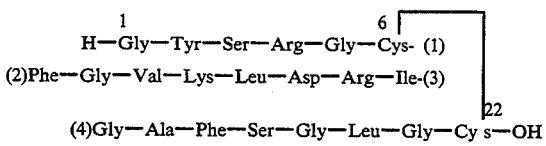

wherein (1) and (2), (3) and (4) directly bind, and the cystein residues (Cys) at positions 6 and 22 form an intramolecular disulfide bond (see SEQ ID NO.:1).

EXAMPLE 3

Biological characteristic of fCNP

A. Relaxant activity of fCNP in chicken rectum

Relaxant activity in chicken rectum was measured in accordance with the method of Kangawa and Currie (Kangawa, K. and Matsuo, H., Biochem. Biophys. Res. Commun., 118, 131–139, 1984; Currie, M. G., Geller, D. M., Cole, B. R., Boylar, J. G., Yusheng, W., Hormberg, S. W. and Needleman, P. Science, 221, 71–73, 1983). The values are averages of six repeats. The results are shown in Table 2. in this assay system, fCNP exhibited an activity which was higher than α-hANP and fANP-21, by about 3 to 7 times, respectively. Although fCNP lacked the tail sequence at the C-terminal which had been considered to be important for analog peptides in displaying biological activities such as diuretic action (Watanabe, T. X., Noda, Y., Chino N., Nishiuchi, Y., Kumura, T., Sakakibara, S. and Imai, M. Eur. J. Pharmacol., 147, 49–57, 1988), fCNP had a strong relaxant activity which was comparable to pCNP (porcine-derived CNP).

TABLE 2

| diuretic peptide | relative activity |
|---|---|
| α-hANP | 100 |
| fCNP | 321 |
| fANP-21 | 47 |
| fANP-24 | 3.7 |
| pCNP | 472 |
| pBNP-26 | 270 |

Relative activity is defined as the activity of equimolar amount of peptides when the activity of α-hANP is 100.

B. Natriuretic action and vasodepressor activity of fCNP

Diuretic action of fCNP was measured in accordance with the method described in Kangawa et al and Sudoh et al (Kangawa, K. et al., Biochem. Biophys. Res. Commun., 118, 131–139, 1984; Sudoh, T., Kangawa, K., Minamino, N. and Matsuo, H. Nature, 332, 78–81, 1988). Male SD rats (weight 300–400 g) were anesthetized by intraperitoneally receiving 50 mg/kg pentobarbital, and a tracheal cannula (PE-240, Cray Adams) was provided to secure an airway. A cannula for measuring the blood pressure (PE-50) was inserted into one of the femoral arteries, and Ringer solution was injected through a cannula (PE-10) inserted into the femoral venous, at a constant rate of 1.8 ml/hr. Urine was collected into a test tube through a bladder cannula of silastic tube (inside diameter 0.02 inch, outside diameter 0.037 inch, Dow Corning). The collection of urine was carried out for 15 min before the administration of the peptides, at 5 min intervals after the administration till 15 min, and then at appropriate time intervals. The effect of the peptides was measured by comparing the amount of the urine samples and the concentration of the electrolyte in the urine samples, as well as by the change of the blood pressure.

In the above assay, a predetermined amount of fCNP was dissolved in 0.1N acetic acid, and neutralized with one tenth volume of 1.3M Tris solution. Then, the solution was diluted with 50 μl of a sterile physiological water, and administered through the cervical vein. As shown in Table 3, the results indicate that fCNP exhibits natriuretic and vasodepressor actions, and further that these actions increase dose dependently.

The natriuretic and vasodepressor actions of fCNP is shown in Table 3, by comparison with α-hANP.

TABLE 3

| peptide | the amount of administration (μg/kg) | excretion | | | |
|---|---|---|---|---|---|
| | | urine (%) | Na+ (%) | K+ (%) | Cl− (%) |
| α-hANP | 3.0 | 461 ± 51 | 572 ± 84 | 291 ± 19 | 445 ± 67 |
| fCNP | 30 | 192 ± 51 | 184 ± 26 | 163 ± 54 | 193 ± 50 |
| | 100 | 315 ± 24 | 344 ± 36 | 217 ± 58 | 251 ± 43 |
| | 300 | 410 ± 27 | 428 ± 29 | 210 ± 33 | 369 ± 6 |

In Table 3, diuretic and natriuretic responses are shown in terms of the amount of the urine, the percentages in the decreases of the excretion of Na+, K+ and Cl− (Means±S.E.M.), in which urine samples were collected separately over 15 min before and after the intravenous injection of the peptides to anesthetized rats. Three rats were used for each peptide.

Diuretic and natriuretic actions of fCNP were lower by about 1/100 compared to that of α-hANP. In anesthetized rats, fCNP also exhibited a weak vasodepressor action. In a typical experiment, the blood pressure at the contract phase of heart was decreased by about 25-30 mg over a period of 30 min by the action of 10 nmol of fCNP. These results are very similar to those of pCNP (Sudoh, T., Minamino, N., Kangawa, K. and Matsuo, H. *Biochem. Biophys. Res. Commun.*, 168, 863–870, 1990).

The present inventors succeeded in isolating and characterizing a novel biologically actlye peptide (fCNP) from frog brains by monitoring relaxant activity in chicken rectum, found that the peptide had a natriuretic action and a vasodepressor action, and further clarified that the peptide was a new peptide which belonged to CNP.

By the isolation and characterization of fCNP, frog and mammal are found to have CNPs in common as well as ANPs. This indicates that both peptides ANP and CNP have been playing a key role in regulating the homeostatic balance of the body fluid volume and the blood pressure since the early stages of the evolution.

It should be noted that the concentration of fCNP in the brain tissue (50 pmol/g wet weight) is much higher than that of ANP and BNP in mammal brains. This indicates that CNPs act mainly oil the nerve transmission system in the brain, and participate in the regulation off the homeostatic balance of body fluid volume and blood pressure in vivo, although the amount of fCNP in the atrium has not been determined at present (as described above, although ANP and BNP exist in the brain and the atrium of mammals, their amount in the atrium has been found to be much higher than that in the brain. In porcine brain, the amount of CNP is nearly equal to that of BNP, and twenty times higher than that of ANP.). Since the structure of fCNP has been clarified herein, it is expected that the correlation between the structure and the activity of CNPs may be elucidated by comparing the primary amino acid sequence of fCNP with porcine brain CNP (pCNP) which was already clarified by the present inventors.

As described above, the present invention will contribute to elucidating the physiological role of fCNP as well as the regulation mechanisms of the homeostatic balance of body fluid volume and the blood pressure in vivo.

---

What is claimed is:

1. An isolated biologically active peptide having the formula:

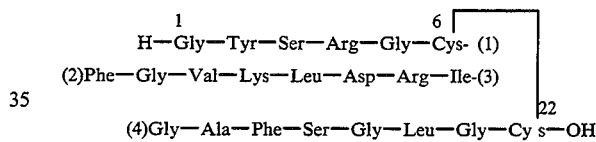

wherein (1) and (2), (3) and (4) directly bind, and the cystein residues (Cys) at positions 6 and 22 form an intramolecular disulfide bond, and an acid addition salt thereof (see SEQ ID NO:1).

* * * * *